United States Patent [19]

Smith et al.

[11] Patent Number: 4,534,939
[45] Date of Patent: Aug. 13, 1985

[54] GAS FLOW CARTRIDGE WITH IMPROVED COAGULATION DETECTION AND EXPANDED ANALYTICAL TEST CAPABILITY

[75] Inventors: Leland B. Smith, Englewood; Jacqueline J. Jackson, Denver, both of Colo.

[73] Assignee: Hemotec, Inc., Englewood, Colo.

[21] Appl. No.: 434,558

[22] Filed: Oct. 15, 1982

[51] Int. Cl.³ ............................................. G01N 33/48
[52] U.S. Cl. ........................................ 422/61; 422/101; 422/73; 73/64.1; 436/69
[58] Field of Search ................................. 422/100–103, 422/57, 58, 61, 73, 119, 44; 436/69, 165, 809; 73/64.1, 57; 435/13; 210/918; 356/39

[56] References Cited

U.S. PATENT DOCUMENTS

| | | | |
|---|---|---|---|
| 3,775,339 | 11/1973 | Kasulin et al. | 252/361 |
| 4,058,367 | 11/1977 | Gilford | 422/63 |
| 4,074,971 | 2/1978 | Braun et al. | 436/69 |
| 4,332,264 | 6/1982 | Gortz et al. | 134/57 R |

Primary Examiner—Barry S. Richman
Assistant Examiner—Joseph P. Carrier
Attorney, Agent, or Firm—John R. Ley

[57] ABSTRACT

A gas flow cartridge includes a tube-like member which defines a reaction chamber in which a pool of liquid is subjected to an analytical test. A coating of debubbling agent is applied to an area of the tube-like member above the reaction chamber. The debubbling agent collapses bubbles of noncoagulated fluid but allows bubbles of coagulated fluid to continue an upward movement above the area where the coating is applied. Coagulation is detected by sensing the coagulated bubbles moving upward in the tube-like member. A quantity of activator agent is initially confined with the reaction chamber, preferably within a structure defined by a segment of paper-like material formed into an activator retaining form. The paper-like material unrolls or unfolds during the analytical test.

25 Claims, 16 Drawing Figures

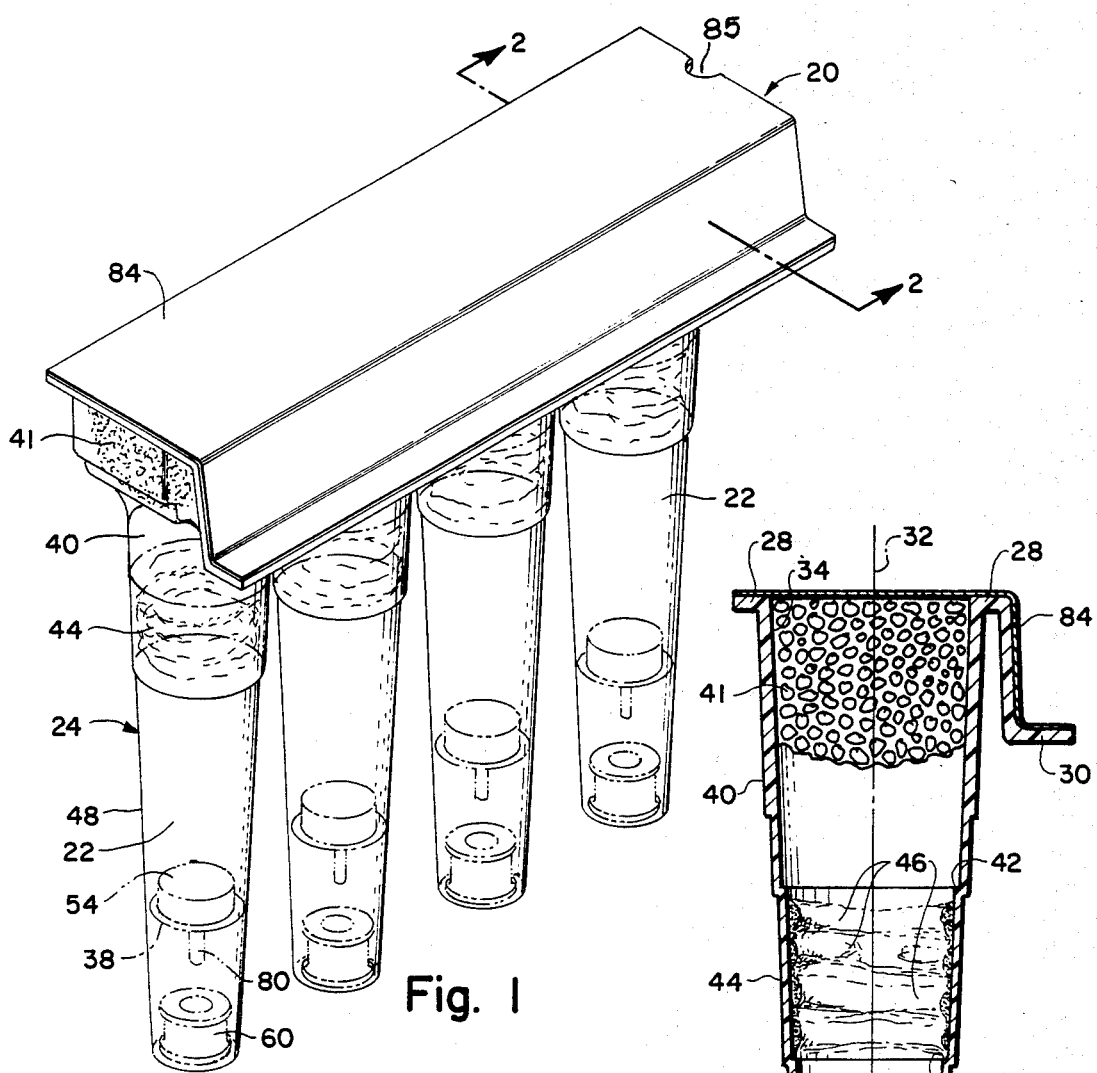
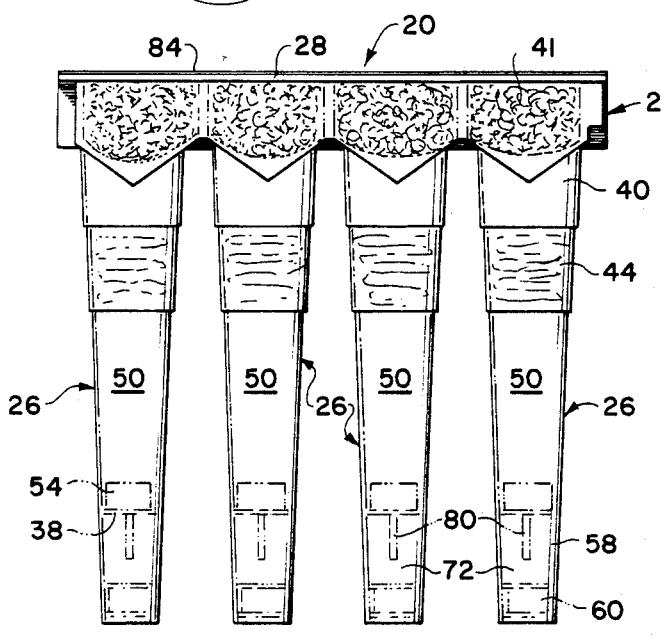
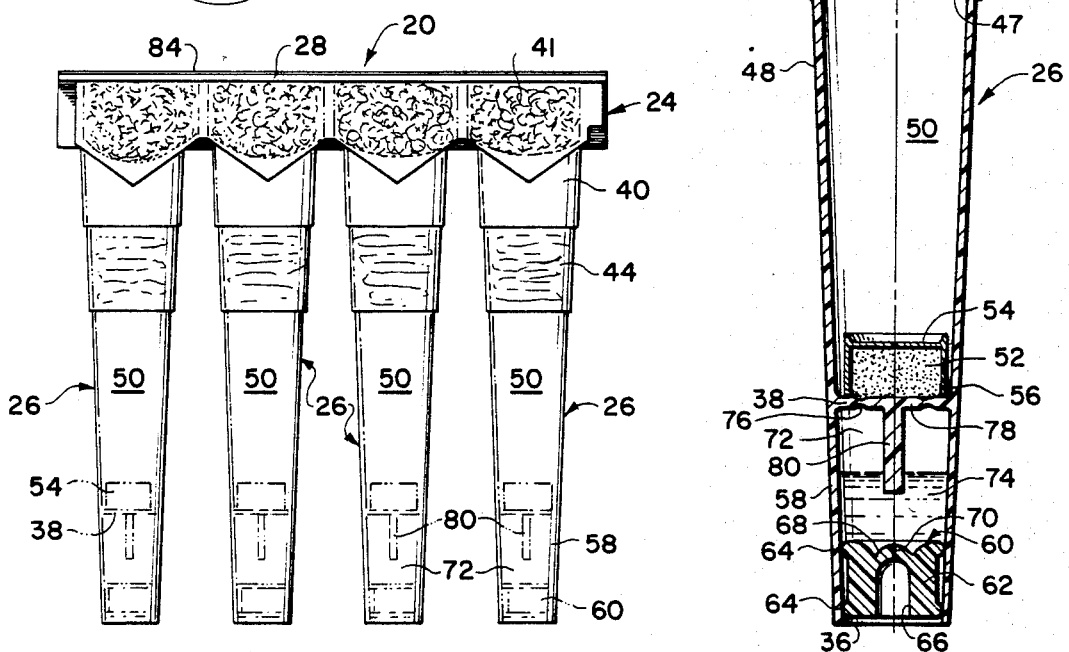
Fig. 1
Fig. 3
Fig. 2

GAS FLOW CARTRIDGE WITH IMPROVED COAGULATION DETECTION AND EXPANDED ANALYTICAL TEST CAPABILITY

This invention pertains to the detection of coagulation and coagulation-related factors in fluid, particularly human blood. More particularly, the present invention pertains to improvements in the type of gas flow analytical cartridge disclosed in U.S. Pat. No. 4,074,971 for Apparatus and Method for the Pharmacological Manipulation of the Coagulation Mechanism in Blood and for Signalling the Event of Blood Coagulation, which is used in apparatus disclosed in U.S. Pat. No. 4,000,972 for Measuring System for the Pharmacological Manipulation of the Coagulation Mechanism in Blood and for the Elapsed Coagulation Time, both of which are assigned to the assignee of the present invention.

Even more specifically, the present invention is for an improved gas flow cartridge which is particularly useful for conducting activated clotting time tests and response to anticoagulant tests (dose response tests), as well as anticoagulant/neutralizing agent titration tests, on human blood to which relatively high therapeutic medical dosages of anticoagulant have been administered, such as, for example, in preparation for and during surgery in which extracorporeal circulation is established.

Titration tests are used to obtain quantitative information on the amount of anticoagulant, typically heparin, which is present in blood. Because of individual responses to heparin and its absorption by human organs, the amount of anticoagulant in the blood of a patient may vary from time to time during surgery and during postoperative recovery. During surgery requiring extracorporeal circulation, it is important to maintain extending clotting times within a relatively wide range, e.g., five to ten minutes. During postoperative recovery, the anticoagulant should be substantially neutralized to restore the near-normal clotting capability to the blood to facilitate healing. Titration tests basically involve mixing a number of different quantities of neutralizing agent with samples of anticoagulated blood and observing which mixture is the first in time to coagulate. Coagulation occurs first in the mixture where the neutralizing agent most totally neutralizes the anticoagulant in the blood. By knowing the amount of neutralizing agent, the amount of anticoagulant or heparin in the blood can be determined. Titration tests do not require measurements of elapsed times, since it is sufficient to know only which mixture is first to coagulate. In titration tests, the cartridge disclosed in U.S. Pat. No. 4,074,971 has proved very successful.

It is currently regarded as desirable to have the capability to conduct activated clotting time and dose response analytical tests, as well as titration tests, on a selective basis under conditions which obtain the test results relatively rapidly and with uniform consistency and reliability. Activated clotting time tests involve the addition of an activator agent such as diatomaceous earth, Celite, or other particulate or chemical activator, to the blood sample to speed up coagulation. The laboratory test protocol with which physicians are primarily familiar for activated clotting time tests is basically a laboratory procedure involving the mixture of blood with a quantity of particulate activator in a test tube, manipulating the test tube, visually detecting the end point of coagulation, and measuring the time for the test until clotting is detected. Laboratory tests are, however, subject to variable results introduced by individual differences in laboratory technique. It is for this reason that more precision uniform testing techniques are desired, such as those supplied by apparatus which uniformly and consistently performs its desired functions. It is also important to maintain, in the automated system, as much relationship as possible to the laboratory test protocol, since the results from the laboratory tests are those with which physicians are primarily familiar. Although there are a number of different types of automated devices for measuring elapsed times for coagulation-related blood tests, such apparatus operate on principles which are substantially different from the laboratory test protocol and the results are therefore not regarded as desirable by most physicians.

Both dose response and activated clotting time tests require the measurement of elapsed time. It is therefore important that end point coagulation be detected in a reliable, consistent and sensitive manner since the measurement of the elapsed time depends upon detection of coagulation.

INVENTION SUMMARY

The improved gas flow cartridge of the present invention can be used to conduct activated clotting time tests, dose response tests, and titration tests on samples of blood which have been treated with anticoagulant. Substantial improvements in the sensitivity and ability to detect end point coagulation are also available from the present gas flow cartridge. Reliable, consistent and accurate results are obtained in all three types of analytical tests when the improved gas flow cartridge is used with an automated actuator mechanism and system such as that disclosed in U.S. Pat. No. 4,000,972.

In accordance with its principal aspects, the improved gas flow cartridge of the present invention comprises a tube-like member defining a reaction chamber in which to hold a pool of liquid such as human blood during a coagulation test and a quantity of activator agent located within the reaction chamber. The quantity of activator agent is preferably retained within a structure formed from a nonfilled fibrous paper-like material which is attached to the tube-like member. A flat segment of paper-like material is formed into the structure and is filled with activator agent, prior to being attached within the reaction chamber. The paper-like structure containing the activator agent is unfolded or opened by the liquid inserted into the reaction chamber and by gas flowing through the pool of liquid in the reaction chamber. The cartridge may also be of the type having a partition extending across the interior of the tube-like member at the bottom of the reaction chamber. The partition may include a break-out portion which breaks away at the beginning of the test. The paper-like material snags or holds the break-out portion and prevents it from moving in the reaction chamber under the influence of the gas moving upward through the pool of liquid. The activator agent within the reaction chamber allows the gas flow cartridge to be used in activated clotting time tests and dose response tests, as well as titration tests.

In accordance with another one of its principal aspects, the gas flow cartridge includes a coating of debubbling agent applied to an area of the tube-like member above the reaction chamber. The debubbling agent is effective on contact with noncoagulated fluid in the bubbles to collapse the bubbles and reflow the noncoagulated fluid downward into the pool in the reaction chamber. The debubbling agent is ineffective on coagulated fluid in the bubbles and allows those bubbles formed by coagulated fluid to continue to move upward through the area where the debubbling agent has been applied. An optical sensor means including a light beam extending through the area of the tube-like member where the debubbling agent has been applied optically senses the presence of the bubbles rising through the area. Coagulation is indicated at an early stage and the detection mechanism of coagulation becomes considerably more sensitive than in prior art arrangements requiring substantial mass transfer of coagulated fluid.

The nature and details of the present invention can be more completely understood by reference to the following description of the preferred embodiment taken in conjunction with the drawings, and from the appended claims.

DRAWING DESCRIPTION

FIG. 1 is a perspective view of an improved gas flow cartridge of the present invention.

FIG. 2 is an enlarged vertical section view taken substantially in the plane of line 2—2 of FIG. 1 along an axis through one of a plurality of test cells of the cartridge shown in FIG. 1.

FIG. 3 is a reduced rear elevational view of the cartridge shown in FIG. 1.

Figure 4:
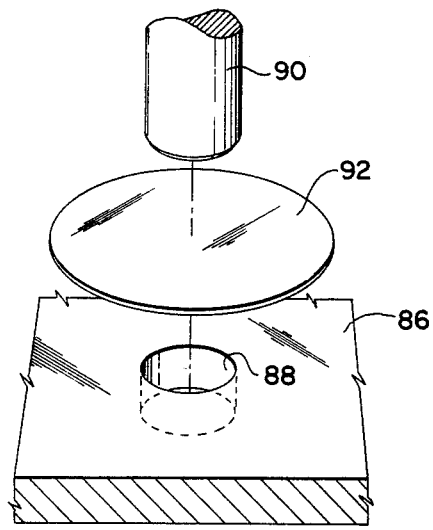
Figure 5:
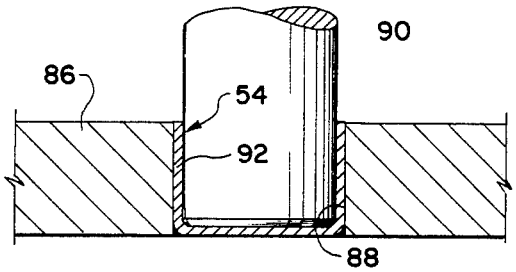
Figure 6:
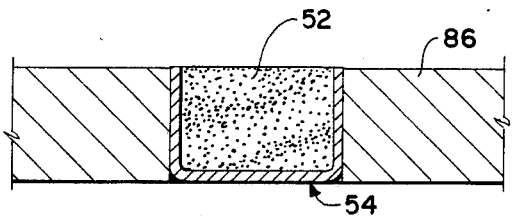
Figure 7:
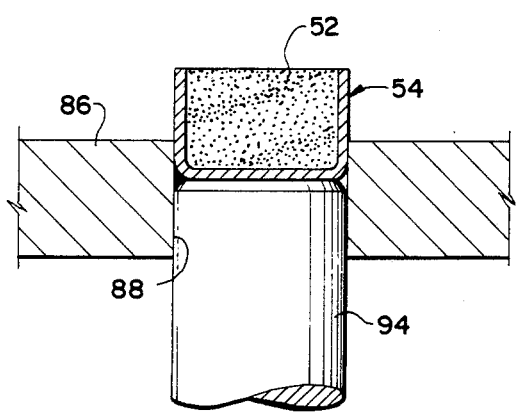

FIGS. 4 through 7 illustrate a method of making a cup-like structure containing an activator agent, which is included in a test cell of the cartridge shown in FIG. 1. Specifically, FIG. 4 is a perspective view of a punch and die with a segment of paper-like material therebetween; FIG. 5 is an enlarged vertical section view illustrating the punch and die set forming the paper-like material into a cup-like structure; FIG. 6 is a vertical section view of the cup-like structure filled with an activator agent; and FIG. 7 is a vertical section view illustrating removal of the cup-like structure filled with activator agent from the die.

Figure 8:
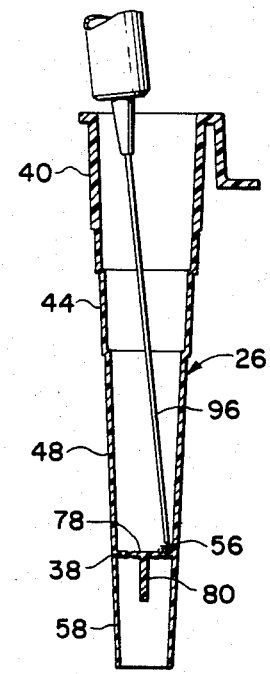

FIG. 8 is a vertically sectioned side view of a tube-like member of the cartridge shown in FIG. 1 illustrating placing a quantity of adhesive in the tube-like member.

Figure 9:
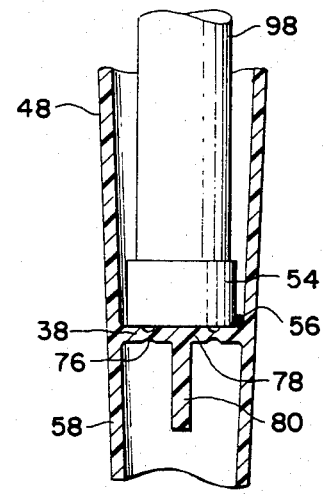

FIG. 9 is an enlarged view of a portion of FIG. 8 at the location where the adhesive has been placed and further illustrating the attachment of the cup-like structure containing the activator agent in an inverted position within the tube-like member.

Figure 10:
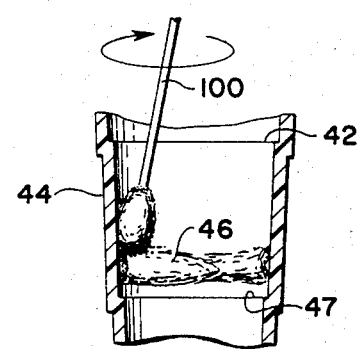

FIG. 10 is an enlarged portion of the tube-like member of the cartridge shown in FIG. 2, illustrating coating an interior wall of the tube-like member with debubbling agent.

Figure 11:
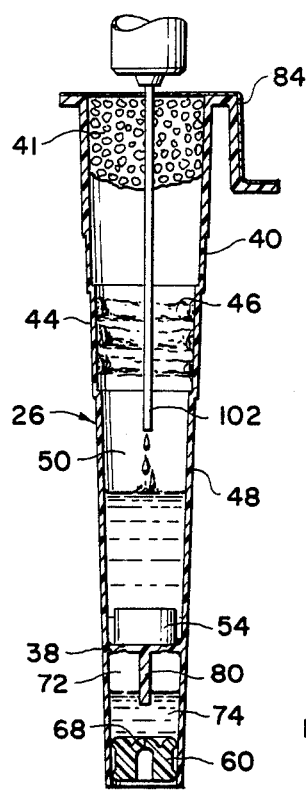
Figure 12:
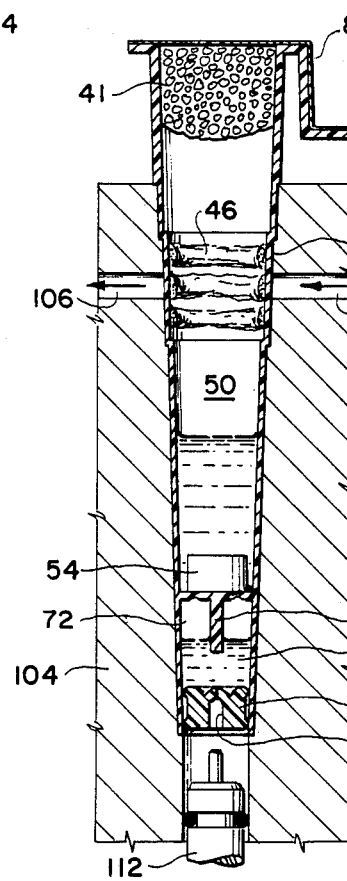

FIG. 11 is a vertical section view similar to FIG. 2 illustrating the addition of a liquid sample within the reaction chamber of the cartridge.

FIGS. 12, 13, 14 and 16 are vertical section views of one tube-like member of the cartridge received within an actuator mechanism, and respectively illustrating the sequence of use of the cartridge.

Figure 15:
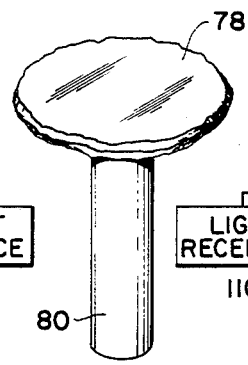

FIG. 15 is a perspective view of a break-away portion and attached pin of each tube-like member of the cartridge.

DETAILED DESCRIPTION

To conduct activated clotting time analytical tests, dose response analytical tests, and titration tests, the improved gas flow cartridge referenced 20 in the drawings is utilized in conjunction with a machine or system such as that disclosed in U.S. Pat. No. 4,000,972. In general as shown in FIG. 1, the cartridge 20 includes a plurality of test cells 22 into which a predetermined quantity or sample of fluid or blood is introduced. A flow of pressurized gas is directed upwardly through the pool of fluid in each of the test cells. The interaction of the gas and the fluid in each test cell creates a rising bubble column in the test cell which provides an indication when coagulation occurs. The actuator mechanism with which the cartridge 20 is utilized recognizes or detects coagulation and provides a measurement of the elapsed time for activated clotting time and dose response tests in one or more or all of the test cells, and provides an indication of the test cell in which coagulation first occurred for titration tests, and other information as is apparent and required from the tests.

The gas flow cartridge 20 is shown in greater detail in FIGS. 1, 2 and 3, and includes a housing 24 preferably formed of integral clear acrylic plastic. Four transversely aligned and vertically oriented tube-like members 26 extend downward from an upper shelf portion 28 of the housing 24. A lip 30 extends downward from the forward edge of the shelf portion 28. The tube-like members 26 are positioned intermediate the front and rear edges of the shelf-like portion and are spaced in transverse alignment in a row and at equal intervals along the transverse dimension of the shelf portion 28. Each of the tube-like members 26 has essentially the same predetermined configuration about an axis 32 which extends through the center of each tube-like member 26.

One tube-like member 26 defines the enclosure of each test cell 22. Each tube-like member 26 has an open upper end 34 and an open lower end 36. A partition 38 which is initially integrally a part of each tube-like member 26, initially divides the interior of the tube-like member into an upper portion and a lower portion which are separated from one another by the integral structure of the partition 38. Subsequently a portion of the partition is broken out to establish fluid communication through the partition.

The structure of each tube-like member 26 above the partition 38 includes an upper portion 40 which extends downwardly from the upper end 34 at the shelf portion 28. The upper portion 40 is generally square in cross section at its upper end and curves downwardly in a transition into its lower end which is cylindrical in cross section. A foam member 41 or, alternatively, a gauze member (not shown) may be confined within the interior of the upper portion 40. An annular shoulder 42 extends radially inward at the lower end of the upper portion 40 and at the upper end of an intermediate frustoconical-shaped portion 44. The intermediate portion 44 tapers slightly radially inward in the downward direction. The interior surface of the intermediate portion 44 has applied thereon a coating 46 of conventional debubbling agent. The coating 46 extends completely around the interior surface to circumscribe a center opening within the hollow interior. It is within the intermediate portion 44 that conditions indicative of coagulation are sensed. The debubbling agent operatively collapses bubbles of noncoagulating fluid to prevent them from rising above the coating and is ineffective on bubbles of coagulating fluid to allow them to rise through the center opening thereby creating conditions indicative of coagulation. An annular shoulder 47 extends radially inward at the lower end of the intermediate portion 44 and at the upper end of a lower portion 48 of the tube-like member above the partition 38. The lower portion 48 is also slightly frustoconically-shaped. The open interior area within the lower portion 48 and above the partition 38 defines a reaction chamber 50 of the cartridge 20.

A quantity of activator agent 52 such as dry diatomaceous earth or Celite is retained within the reaction chamber 50. The activator agent 52 is preferably retained substantially within an enclosure defined by an inverted cup-shaped structure 54. The activator agent 52 is thereby confined between the inverted cup-shaped structure 54 and the partition 38. The cup-shaped structure 54 is glued or otherwise fastened to the interior surface of the lower portion 48 by a spot of adhesive 56.

The lower open portion of the interior of the tube-like member is defined by the partition 38 at its upper end and by a lowermost portion 58 of the tube-like member 26. The lowermost portion 58 terminates at the lower open end 36 of the tube-like member. The interior surface of the lower portion 58 is substantially cylindrical and concentric about the axis 32.

A lower plug member 60, which is formed of resilient, flexible material such as Kraton, is frictionally received within the lower open interior of the tube-like member. The lower plug 60 extends across and frictionally engages and seals against the inner cylindrical surface of the lowermost portion 58. The plug member 60 includes a generally cylindrical main body portion 62 from which a pair of ring-like annular edges 64 protrude outwardly at each axial end of the main body portion 62 and contact the interior side wall of the lowermost portion 58. A center cylindrical opening 66 extends axially through the main body portion 62. An upwardly convex-shaped dome portion 68 extends across the upper axial end of the main body portion 62 and closes the center opening 66 at its upper end. A diametrically extending slit 70 extends completely axially through the dome portion 68 at the axis 32. Normally, the resiliency of the dome portion 68 holds the slit 70 closed and thereby seals the slit 70 against the passage of fluid or other substances therethrough. Additionally, a coating of sealant may be applied to the top surface of the dome portion 68 to further insure closure of the slit 70. The main body portion 62 is slightly radially compressed to develop sufficient retention force to hold the plug member 60 in place in the lower interior opening of the tube-like member.

Initially, the plug member 60 is positioned substantially adjoining the lower open end 36 of the tube-like member. A reagent chamber 72 is defined by the partition 38, the lowermost portion 58 of the tube-like member 26, and the lower plug member 60 in its initial position. Fluid reagent 74 is confined within the reagent chamber 72 prior to use of the cartridge 20. The type of reagent 74 in the reagent chamber 72 determines whether the cartridge 20 is one for use in titration tests, activated clotting time tests, or dose response tests. For titration cartridges, the reagent will typically include a predetermined amount of protamine sulfate and an activator combined in a buffer solution. In activated clotting time cartridges, the reagent may be an activator combined in a buffer solution. In dose response tests, the reagent is a predetermined amount of heparin combined in a buffer solution. To insert the reagent into the reagent chamber 72, the housing 24 is inverted from the position shown in FIG. 2 and the reagent 74 is added into the reagent chamber. A wire is placed alongside the plug member 60 to vent air from the reagent chamber past the annular edges 64 as the plug member 60 slides into the lower interior opening of the tube-like member 26, and then the wire is removed.

The partition 38 which initially seals the reaction chamber 50 from the reagent chamber 72 includes an annular ring 76 of reduced thickness which divides a center disc portion 78 from the remainder of the partition 38. The integral material at the annular ring 76 is adapted to break, thereby separating the center disc portion 78 from the remainder of the partition 38 and thereby create fluid communication between the reagent chamber 72 and the reaction chamber 50. A pin 80 extends integrally downwardly from the center disc portion 78. When the center disc portion 78 is broken out of the partition 38, the pin 80 remains attached to the disc portion 78. FIG. 15 illustrates the pin and disc portion which have been broken away from the partition.

The gauze or foam member 41 retained within the upper portion 40 of the tube-like member 26 is primarily useful in collecting coagulated liquid from the reagent chamber after coagulation occurs. Unlike the function of the gauze or foam member disclosed in the aforementioned U.S. Pat.No. 4,074,971, the foam member 41 does not play a role in detecting coagulation, as it did in the aforementioned patent.

A cover 84 is attached to the upper surface of the shelf portion 28. The cover 84 preferably also extends around and down on the front outer surface of the lip 30. The cover 84 is preferably a single piece of paper and is attached preferably by gluing it around the outer edges of the shelf portion 28 and on the outer front surface of the lip 30. The cover 84 should have characteristics which allow it to be relatively easily penetrated by a syringe needle, to insert the fluid sample within the reaction chamber 50. The cover 84 contains printed indicia indicative of the type of cartridge and analytical test to be conducted with the cartridge. The printed indicia may also indicate the quantities or strengths and types of reagent 74 present in the reagent chamber 72. Additionally, notches 85 (FIG. 1) are formed into one edge of the shelf portion 28, and the position of the notches 85 are mechanically sensed when the cartridge 20 is inserted in the operating machine (not shown). The notches 85 form a code indicative of the type of analytical test to be performed with the cartridge.

Making the cup-shaped structure 54 and filling it with activator agent 52 are illustrated in FIGS. 4, 5, 6 and 7, in sequence. A die 86 having a cylindrical opening 88 formed therein, and a cylindrical punch 90 are provided. A circular disc 92 of cellulose-type filter paper, or other clean nonfilled fibrous material, is inserted over the cylindrical opening 88 between the die 86 and punch 90, as shown in FIG. 4. The punch moves into the die and pulls the paper disc 92 into the cylindrical opening 88, thereby forming the cup-shaped structure 54 from the paper disc 92, as shown in FIG. 5. The diameter of the paper disc 92 is such that the uppermost open ends of the cup-shaped structure 54 terminate at a position approximately level with the top surface of the die 86. The height of the cup-shaped structure and the thickness of the die 86 is also predetermined in order to confine a predetermined quantity or volume of the activator 52 within the cup-shaped structure 54, as shown in FIG. 6. The activator 52 is added to the cup-shaped member 54 until the upper level of the activator 52 is approximately even with the upper surface of the die 86. The activator agent may thereafter be compacted or otherwise firmly retained within the cup-shaped structure. A removal tool 94 pushes the cup-shaped structure 54 and the retained activating agent 52 out of the cylindrical opening 88, as shown in FIG. 7.

To insert the cup-shaped structure 54 and its retained activator agent 52 into the tube-like member 26, adhesive 56 is first applied to the interior surface of the lower portion 48 of the tube-like member 26 at a position adjoining the partition, as shown in FIG. 8. A syringe-like device having a long needle-like delivery tube 96 is placed into the upper open interior of the tube-like member to locate the adhesive 56 in a spot at a position adjoining the partition 38. The cup-shaped structure 54 containing the activator agent 52 is attached in inverted orientation to a positioning tool 98 and the positioning tool 98 places the side wall of the cup-shaped structure 54 in contact with the spot of adhesive 56, as shown in FIG. 9. The activator agent is retained within the cup-shaped structure to prevent it from falling out when the cup-shaped structure is inverted. The cup-shaped structure 54 is released by the positioning tool 98 and the adhesive is allowed to harden. The adhesive is a nonwaterbase adhesive which has sufficient strength to retain the paper disc 92 of the cup-shaped structure 54 to the lower tube-like portion 48 during the analytical test when fluid is in contact with the adhesive.

The coating 46 of debubbling agent is placed on the interior surface of the intermediate portion 44 preferably by use of a swab 100, as illustrated in FIG. 10. The swab 100 is dipped in the debubbling agent and is then moved around the interior surface of the intermediate portion 44 to coat it with the debubbling agent. Of course, the steps of applying the coating 46 and attaching the cup-shaped structure 54 and its retained activator agent in the tube-like member occur prior to insertion of the foam member 41 and attachment of the cover 84 (FIG. 3).

Use of the cartridge 20 and its operative features are illustrated in FIGS. 11, 12, 13, 14 and 16, in sequence. To fill the reagent chamber 50 with a quantity of sample of fluid, preferably human blood, a syringe needle 102 pierces the cover 84 and penetrates through the foam member 41. A predetermined quantity of blood is expelled into the reaction chamber 50 and forms a pool at the bottom of the reaction chambers 50 which engulfs the cup-like structure 54 containing the reagent. Once each of the reaction chambers has been filled with the sample of fluid, the tube-like members 26 of the cartridge are inserted in a receptacle or receiving means generally referenced 104 of an actuator mechanism, such as that disclosed in U.S. Pat. No. 4,000,972.

Figure 16:
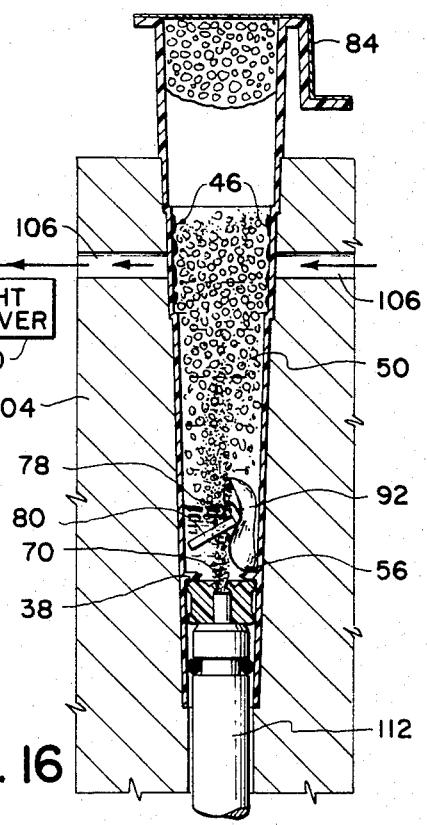

The cartridge receiving means 104 includes passageways 106 formed therein at a vertical level adapted to be approximately midway axially between the upper and lower ends of the intermediate portion 44 of the tube-like member 26 when it is received in the receiving means 104. A light beam from a light source 108 (FIG. 14) is transmitted into the passageway 106 on one side of the tube-like member 26. The light passes through the transparent intermediate portion 44 and experiences very little defraction by the coating 46 of the debubbling agent. The majority of the light continues in the path out of the intermediate portion 44 into the passageway 106 on the opposite side to a light receiver 110 (FIG. 16). Although not shown in FIG. 12, the receiving means also firmly retains the cartridge in position during the test. A nozzle member 112 is operatively positioned below the lower open end of the tube-like member. The nozzle member 112 includes a projection 114 adapted to extend into and seal within the center opening 66 of the lower plug 60.

Figure 13:
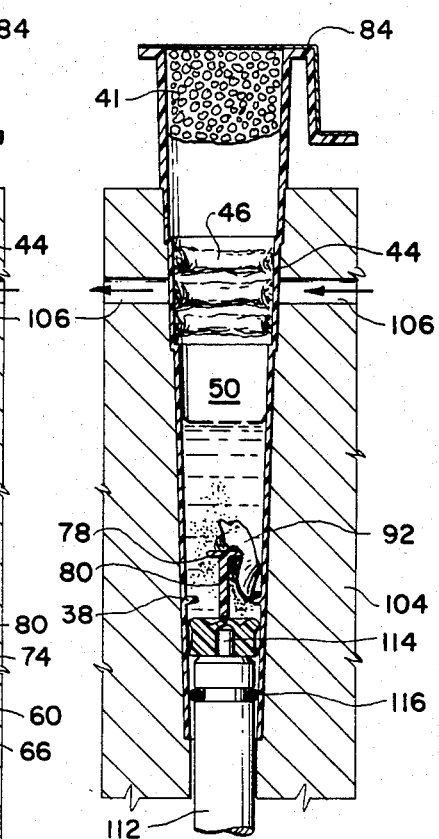

At the start of the analytical test, as shown in FIG. 13, the nozzle member 112 is moved upward. The projection 114 extends into the plug member center opening 66. The plug member 60 is pushed upward along the interior surface of the lowermost portion 58 of the tube-like member 26. The dome portion 68 and projection 114 contact the lower end of the pin 80 and the continued upward movement breaks out the disc portion 78 from the partition 38. The reagent 74 from the reagent chamber 72 is forced into the reaction chamber 50. The upward moving pin and disc portion contact the paper material cup-shaped structure 54. The upward movement of the disc portion and pin and the upward flowing reagent mix the activator agent 52 with the fluid in the reaction chamber 50 and opens the cup-shaped structure by unfolding the paper material. The upward movement of the lower plug member 60 terminates when it contacts the remaining portion of the partition 38. An 0-ring seal 116 of the nozzle member seals against the interior surface of the lowermost portion 58.

Figure 14:
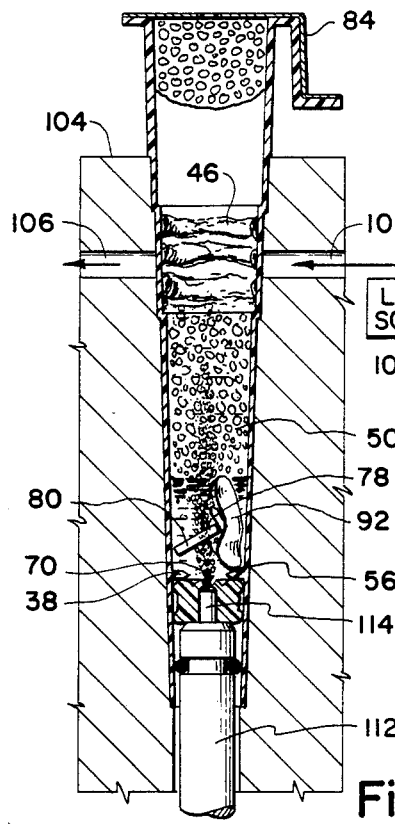

Once the contents of the reagent chamber have been forced into the reaction chamber 50, a flow of pressurized gas is delivered upwardly from the projection 114 of the nozzle member 112, as shown in FIG. 14. Under the force of the pressurized gas delivered, the slit 70 in the dome portion 68 expands to admit the pressurized gas into the fluid of the reaction chamber. The gas flows upward through the pool of liquid at the bottom of the reaction chamber 50. The relatively ragged edge (FIG. 15) of the center disc portion 78 hooks or lodges in the unfolded paper disc 92. The paper disc unfolds under the influence of the upward moving gas, but the adhesive 56 prevents the paper disc 92 from moving upward. In this manner, the disc portion 78 and attached pin 80 are prevented from floating upward and possibly being carried by the bubbles to a position to influence the light beam. The paper material 92 shall have sufficient wet strength to hold the pin 80 and disc portion 78 under these conditions. Gas introduced by the nozzle member flows upward through the foam member 41 and out of the hole formed in the cover 84 by the syringe needle 102 (FIG. 11).

The pressurized gas flowing through the pool of fluid in the reaction chamber causes bubbles of fluid to be carried upward. The bubbles move upward and contact the coating 46 of debubbling agent on the intermediate portion 44 of the tube-like member 26. The debubbling agent becomes effective to immediately collapse bubbles of noncoagulating fluid and reflow or drain the noncoagulating liquid from the bubbles back to the pool in the reaction chamber. The coating 46 of debubbling agent has been found sufficient to prevent the bubbles from rising substantially above the shoulder 47. Bubbles of noncoagulating fluid in the center of the column of bubbles rising upwardly through the reaction chamber are pulled outward by the collapsing bubbles to the side surfaces of the intermediate portion where they too are collapsed by the action of the debubbling agent. Of course, the flow of pressurized gas in the pool of liquid causes mixing of the activating agent 52 and the reagent 74 with the sample of liquid, and also acts somewhat as an activator itself.

When coagulation in the fluid sample commences, as is illustrated in FIG. 16, the coating 46 of debubbling agent is no longer effective to collapse the bubbles. The bubbles rise in the column through the intermediate portion 44. The bubbles diminish or diffuse the amount of light received by the light receiver 110. Upon detection of the reduction in intensity of the light beam by a predetermined amount, the light receiver 110 supplies a signal indicative of coagulation. The signal indicative of coagulation is used to terminate the measurement of the total elapsed time for the test in activated clotting time and dose response tests, and is used for the purpose of designating the test cell in which coagulation first occurred in titration analytical tests.

After termination of the analytical test, the nozzle member 112 is withdrawn downward and the slit 70 is closed by the resiliency of the dome portion 68 to confine the contents within the reaction chamber.

Substantial improvements result by coating the intermediate tube-like portion 44 with debubbling agent and sensing coagulation when bubbles rise through the intermediate portion, as compared to the detection arrangement disclosed in the aforementioned U.S. Pat. Nos. 4,000,972 and 4,074,971. In both of the aforementioned patents, detection of coagulation was achieved when the level of the liquid fluid in the reaction chamber dropped due to the accumulation of coagulating fluid transported by the bubbles to the gauze member during coagulation. Before coagulation was indicated, this arrangement required the transportation of a considerable mass of fluid out of the reagent chamber. In some situations, rapid massive clotting occurred in the reaction chamber before the fluid could be transported upward. Of course, when massive clotting occurred, it was impossible to detect a drop in level in the reaction chamber. By the present invention, detection occurs more precisely and quickly because the column of bubbles rises into the intermediate tube-like portion 44 relatively rapidly and without carrying considerable mass once coagulation commences. The coating 46 of debubbling agent is very effective in confining the upper level of the bubble column below the intermediate portion prior to coagulation. Thus, a change of conditions is readily detected and results are obtained very quickly after the onset of coagulation. The activator agent is conveniently confined in the reaction chamber in a position and by means which allow it to be rapidly dissipated and mixed with the fluid sample. The paper material forming the cup-like structure effectively snags and holds the pin and disc portion and prevents it from moving about in the reaction chamber during the course of the analytical test. Many other advantages are also apparent.

The nature and operation of the present invention has been shown and described with a degree of specificity. It should be understood, however, that the specificity of the description has been made by way of preferred example and that the invention is defined by the scope of the appended claims.

What is claimed is:

1. In a cartridge defining a reaction chamber in which to hold a pool of blood or a blood derivative during a coagulation analytical test, a reagent chamber to hold a liquid reagent, means separating the reaction chamber and the reagent chamber, and means for intercommunication of the reaction chamber and the reagent chamber, an improvement comprising:

means containing a pre-determined quantity of activator agent within the reaction chamber said means being designed to release the activator agent into the blood or the blood derivative when the reaction chamber is intercommunicated with the reagent chamber to intermix the reagent with the pool of blood or the blood derivative.

2. A cartridge as defined in claim 1 wherein said reaction chamber is part of an upwardly extending tube-like member for receiving the liquid pool and wherein an area of the interior surface of the tube-like member located above the reaction chamber is coated with a debubbling agent, the coated area of debubbling agent operative to collapse bubbles of noncoagulated fluid and prevent the bubbles of noncoagulated fluid from moving past the coated area, and the coated area being ineffective on bubbles of coagulated fluid.

3. A cartridge as defined in claim 1 wherein said cartridge is an upwardly extending tube-like member which defines the reaction chamber and receives the liquid pool and further including means for admitting gas flowing upwardly through the liquid pool in the reaction chamber to create bubbles and to transport liquid in the bubbles through the tube-like member above the pool and the reaction chamber, and wherein said means containing the predetermined quantity of activator agent includes a flat segment of fibrous paper-like material which is initially formed into a cup-like structure for containing the quantity of activator agent, and further comprising means attaching the cup-like structure to the tube-like member at a position adjacent the lower portion of the reaction chamber.

4. A cartridge as defined in claim 3 wherein the segment of fibrous paper-like material is adapted to open from the cup-like form under the influence of the liquid in the reaction chamber and the flow of gas through the pool of liquid.

5. A cartridge as defined in claim 9 and further of the type having a partition extending across the open interior of the tube-like member at the bottom of the reaction chamber, the partition including a break-out portion, and wherein the paper-like material operatively snags or holds the break-out portion after it is broken out of the partition.

6. In a gas flow cartridge having an upward extending tube-like member defining a reaction chamber in which to hold a pool of fluid during a coagulation analytical test, and means for admitting gas flowing upward through the liquid pool to transport liquid in bubbles from the pool above the reaction chamber upward through a hollow interior of the tube-like member, an improvement comprising:

a coating of debubbling agent applied to the interior of the tube-like member at a location above the reaction chamber and over an area extending completely around the periphery of the interior to circumscribe a substantially unobstructed center opening in the hollow interior through which bubbles of fluid may pass, the coating of debubbling agent being effective on contact with noncoagulated fluid in the bubbles to collapse all the bubbles of noncoagulated fluid within the center opening and reflow the noncoagulated fluid downward into the pool in the reaction chamber and prevent the upward movement of bubbles of noncoagulated fluid through the center opening, the coating of debubbling agent further being ineffective on coagulated fluid in the bubbles to allow the bubbles of coagulated fluid to continue upward through the center opening.

7. A cartridge as defined in claim 6 in combination with transmitting means for directing a light beam within the tube-like member in the area where the debubbling agent has been applied, the light beam being of the type having characteristics which are modified by bubbles of liquid intersecting the beam, and receiving means for receiving the modified light beam after it emerges from within the tube-like member in the area where the debubbling agent has been applied and for detecting modifications of the light beam caused by bubbles of coagulated fluid passing through the area where the debubbling agent has been applied.

8. A cartridge as defined in claim 6 in combination with optical sensor means for sensing the presence of bubbles of coagulated fluid in the tube-like member within the area where the debubbling agent has been applied.

9. A cartridge as defined in claim 6 further comprising a quantity of activator agent retained in the reaction chamber.

10. A cartridge as defined in claim 6 and further of the type having a reagent chamber within the tube-like member below the reaction chamber, and wherein the reagent chamber initially confines therein a quantity of an activator agent.

11. A cartridge as defined in claim 6 and further of the type having a housing of which the tube-like member is a part, and wherein the housing includes a shelf portion from which the tube-like member extends downward, and at least one notch formed in a side of the shelf portion defining a code indicative of the type of analytical test to be conducted with the cartridge.

12. A cartridge as defined in claim 6 in combination with transmitting means for directing a light beam within the hollow interior, the light beam being of the type having characteristics which are modified by bubbles of liquid intersecting the beam, the light beam passing within the hollow interior of said tube-like member at a predetermined position relative to the coating to detect bubbles of coagulated fluid rising through the center opening circumscribed by said coating, and receiving means for receiving the light beam and for detecting modifications of the light beam caused by bubbles of coagulated fluid passing through the center opening.

13. A cartridge as defined in claim 6 in combination with optical sensor means for sensing the presence of bubbles of coagulated fluid in the tube-like member rising through the center opening.

14. A cartridge as defined in claim 6 and further of the type comprising means located at the upper end of the hollow interior for collecting coagulated fluid transported thereto by bubbles rising through the hollow interior, and wherein the coating is located intermediate the reaction chamber and the coagulated fluid collecting means.

15. A cartridge as defined in claim 6 further comprising an enclosure containing a quantity of activating agent, and means for retaining the enclosure to the tube-like member within the reaction chamber.

16. A cartridge as defined in claim 15 wherein the enclosure is substantially defined by a paper-like material, and the paper-like material is attached to the tube-like member within the reaction chamber.

17. A cartridge as defined in claim 16 wherein the paper-like material is initially in a cup-shaped form, and the paper-like material opens from the cup-shaped form after insertion of the fluid sample in the reaction chamber and flowing of gas through the pool of fluid.

18. A cartridge as defined in claim 17 and further of the type having a partition extending across the open interior of the tube-like member at the bottom of the reaction chamber, the partition including a break-out portion, and wherein the paper-like material operatively snags or holds the break-out portion after it is broken out of the partition, the paper-like material having sufficient wet strength to avoid tearing under the influence of gas passing thereover while holding the break-out portion during the test.

19. A cartridge as defined in claim 18 and further of the type having a reagent chamber within the tube-like member below the partition and a lower plug member movably received within the tube-like member and sealing the lower end of the reaction chamber, the lower plug member initially spaced from the partition to define a predetermined volume within the reagent chamber for containing reagent chamber contents therein, the plug-like member having a dome portion defining a selectively openable and closable slit therethrough, the break-out portion of the partition having a pin extending downwardly therefrom and adapted to be contacted by the plug member as the plug member is moved upwardly in the reagent chamber to break out the break-out portion, the upward movement of the plug member also forcing the contents of the reagent chamber into the reaction chamber by reducing the predetermined volume.

20. A cartridge as defined in claim 19 wherein the activator agent is one of a particulate or chemical activator.

21. In a gas flow cartridge having an upward extending tube-like member and a partition extending across the open interior of the tube-like member to define a reaction chamber and a reagent chamber within the interior of the tube-like member which are respectively above and below the partition, means associated with the partition for initially sealing an opening through the partition and for selectively thereafter being removed to provide fluid communication through the partition between the reaction and reagent chambers, the reaction chamber operatively holding a pool of liquid during a coagulation analytical test, and means for admitting gas flowing upward through the liquid pool in the reaction chamber to create bubbles and to transport liquid in bubbles through the tube-like member above the pool and reaction chamber, and an improvement comprising a segment of fibrous material formed into a predetermined structure and attached to the tube-like member within the reaction chamber at a position adjacent the partition, the fibrous material adapted to open from the initial structural form and snag or hold the initial sealing means after being selectively removed from the partition.

22. A cartridge as defined in claim 21 wherein the initial sealing means includes a break-out portion of the partition which is broken out and separated from the remaining part of the partition to form the opening through the partition.

23. A cartridge as defined in claim 21 wherein the initial structure of the fibrous material retains therein a predetermined quantity of activator agent.

24. A cartridge as defined in claim 23 wherein an area of the interior surface of the tube-like member located above the reaction chamber is coated with debubbling agent.

25. A cartridge as defined in claim 24 wherein the coated area of debubbling agent is operative to collapse bubbles of noncoagulated fluid and prevent the bubbles of noncoagulated fluid from moving past the coated area, and the coated area being ineffective on bubbles of coagulated fluid.

* * * * *